(12) United States Patent
Campian et al.

(10) Patent No.: US 6,583,318 B2
(45) Date of Patent: Jun. 24, 2003

(54) METHOD FOR SYNTHESIS OF α-SULFONAMIDO AMIDE, CARBOXYLIC ACID AND HYDROXAMIC ACID DERIVATIVES

(75) Inventors: Eugene Campian, Louisville, KY (US); Boliang Lou, Louisville, KY (US); Adnan M. M. Mjalli, Jamestown, NC (US)

(73) Assignee: Advanced Syntech, LLC, Louisville, KY (US)

( * ) Notice: Subject to any disclaimer, the term of this patent is extended or adjusted under 35 U.S.C. 154(b) by 0 days.

(21) Appl. No.: 10/146,713

(22) Filed: May 15, 2002

(65) Prior Publication Data

US 2003/0013910 A1 Jan. 16, 2003

Related U.S. Application Data

(60) Provisional application No. 60/291,258, filed on May 17, 2001.

(51) Int. Cl.[7] ............... C07C 303/00; C07C 307/00; C07C 309/00; C07C 311/00; C07C 321/00; C07C 323/00; C07C 381/00

(52) U.S. Cl. ............... 564/86; 564/80; 564/84; 564/85; 564/86; 564/87; 564/88; 564/89; 564/90; 564/91; 564/92; 564/93; 564/94; 564/95; 564/96; 564/97; 564/98; 564/99

(58) Field of Search ............... 564/86, 80, 84, 564/85, 87, 88–99

(56) References Cited

U.S. PATENT DOCUMENTS

| 5,607,954 A | 3/1997 | Weidmann et al. |
|---|---|---|
| 5,637,586 A | 6/1997 | Yanaka et al. |
| 6,300,368 B1 | 10/2001 | Yamashita et al. |

*Primary Examiner*—Samuel Barts
*Assistant Examiner*—Elvis O. Price
(74) *Attorney, Agent, or Firm*—Stites & Harbison PLLC; John E. Vanderburgh

(57) ABSTRACT

A method of synthesizing α-sulfonamido amide, carboxylic acid or hydroxamic acid derivatives comprising providing a set of polymer-bound reactant(s) (sulfonamide, aldehyde or ketone, isocyanide or acid) to react with three sets of the other three reactants to form an array of polymer-bound α-sulfonamido amide-type intermediates and use of such intermediates for the preparation of combinatorial libraries.

6 Claims, 4 Drawing Sheets

2-1

$R_1$, or $R_2$, or $R_5$ is attached to solid support, then base treatment

4-1

N-alkylation
e.g., Mitsunobu reaction

4-2

$R_1$, or $R_2$, or $R_5$ is attached to solid support

Cleavage

4-3

METHOD FOR SYNTHESIS OF α-SULFONAMIDO AMIDE, CARBOXYLIC ACID AND HYDROXAMIC ACID DERIVATIVES

CROSS REFERENCE TO RELATED APPLICATION

This application claims the benefit of the filing date of Provisional Application Ser. No. 60/291,258, entitled METHOD FOR SYNTHESIS OF ALPHA-SULFONAMIDO CARBOXYLIC ACID AND HYDROXAMIC ACID DERIVATIVES, filed May 17, 2001 in the name of Campian et al.

FIELD OF INVENTION

The present invention relates to a novel method for solid phase synthesis of diverse sulfonamido amide, carboxylic acid and hydroxamic acid derivatives, and the use of such a method to create combinatorial libraries of diverse sulfonamido amides, carboxylic acids and hydroxamic acids.

BACKGROUND OF THE INVENTION

Sulfonamido carboxylic acids and their derivatives are widely used as building blocks in the design and synthesis of biologically active peptidomimetics, such as sulfonamide peptoids. α-Sulfonamido carboxylic acids and the corresponding hydroxamic acid derivatives are also an important class of matrix metalloprotease inhibitors which have recently received great attention as therapeutic agents for the treatment of human diseases. Several α-sulfonamido hydroxamic acids are currently under clinical investigation against arthritis and cancer.

Conventional approaches to the preparation of the sulfonamido acid derivatives rely on the use of amino acids as the starting material followed by N-sulfonylation. However, the process can be tedious if the amino acids to be used are not readily available although a great deal of efforts have been made during the last three decades in the development of efficient methods for the synthesis of unnatural amino acid derivatives.

Based on the usefulness of the above-described compounds, if would generally be advantageous to have methods of rapidly and efficiently synthesizing structurally diverse derivatives of these compounds, as well as libraries containing large numbers of these compounds. The present invention meets these and other needs.

The importance of multi-component reactions (MCR) has been demonstrated in the synthesis of various classes of organic molecules, especially in the area of combinatorial synthesis. These reactions enable to assemble three or more different building blocks, in most cases, in a single chemical process. The Ugi condensation reaction employs four components including a carboxylic acid, an amine, an aldehyde and an isocyanide to construct an α-acylaminoamide which can be transferred into the corresponding amino acid, ester and etc. The versatility of the reaction has also been demonstrated in the solid phase synthesis of a variety of biologically interesting structures by post Ugi transformations.

The methods of the invention employ a multi-component condensation reaction for the construction of the key intermediates on solid supports.

SUMMARY OF INVENTION

The invention is generally directed to novel methods of synthesizing diverse α-sulfonamido amide, carboxylic acid and hydroxamic acid derivatives. Typically, the methods of the invention employ a multi-component condensation reaction for the construction of the key intermediates on solid supports. Instead of amines (e.g., alkyl amine or aniline), according to the invention sulfonamides are the first time employed in the four-component condensation reaction. This four-component reaction (a sulfonamide, an aldehyde or ketone, an isocyanide and an acid) enables one to generate a sulfonamido amide-type intermediate in one-step on solid support (FIGS. 1 and 2).

Either of the four components can be attached to the solid support, which reacts with other three reagents (FIG. 2). Further chemical manipulation, such as treatment with a base to remove the acyl moiety followed by N-alkylation, such as the Mitsunobu reaction, gives polymer-bound products, which are then cleaved on the solid support under various cleavage conditions.

The present invention also provides methods of preparing libraries of diverse α-sulfonamido amide, carboxylic acid and hydroxamic acid derivatives. The method of synthesizing a library of α-sulfonamido amide, carboxylic acid or hydroxamic acid derivatives comprising providing a set of polymer-bound reactant(s) (sulfonamide, aldehyde or ketone, isocyanide or acid) to react with three sets of the other three reactants to form an array of polymer-bound α-sulfonamido amide-type intermediates. Further chemical manipulation may be applied, which comprises the treatment with a base for removal of the acyl moiety and N-alkylation gives polymer-bound highly functionalized products. A library of the diverse products is then released from the solid support under various cleavage conditions.

DETAILED DESCRIPTION OF INVENTION

Figure 1:
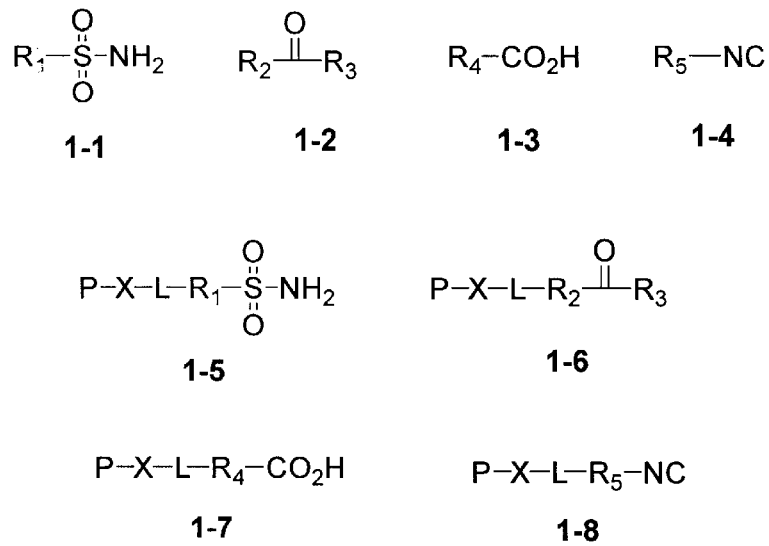
FIG. 1 illustrates the four components of the condensation reaction and corresponding polymer bound forms.

FIG. 1 illustrates the four components (sulfonamide of formula 1-1, aldehyde or ketone of formula 1-2, carboxylic acid of formula 1-3 and isocyanide of formula 1-4) utilized in the condensation reactions. The corresponding polymer-bound forms are presented as formula 1-5, 1-6, 1-7 and 1-8, respectively.

Figure 2:
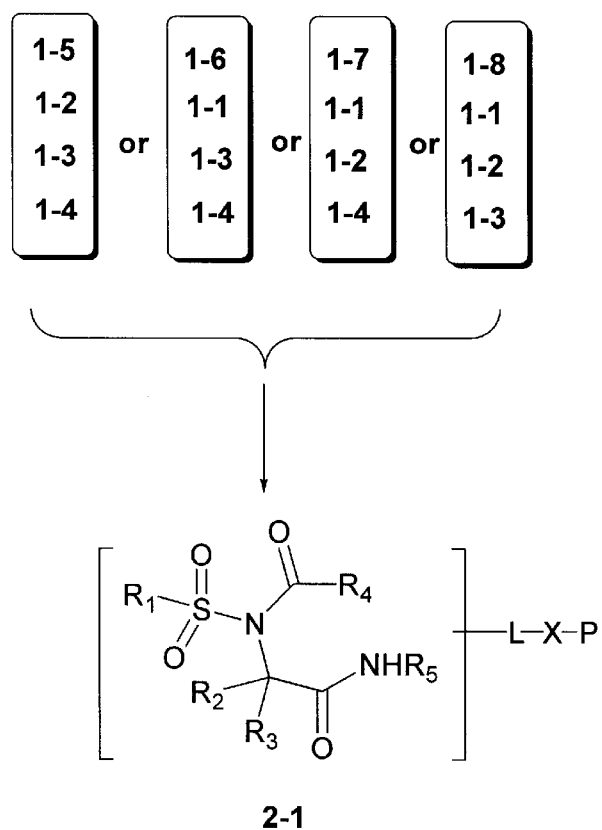
FIG. 2 illustrates the solid phase four-component condensation reaction utilizing one of the polymer-bound components.

FIG. 2 illustrates the solid phase four-component condensation reaction utilizing one of the polymer-bound components (1-5 to 1-8). The newly formed product is described as formula 2-1, wherein $R_1$, or $R_2$, or $R_4$, or $R_5$ is attached to the polymer.

Figure 3:
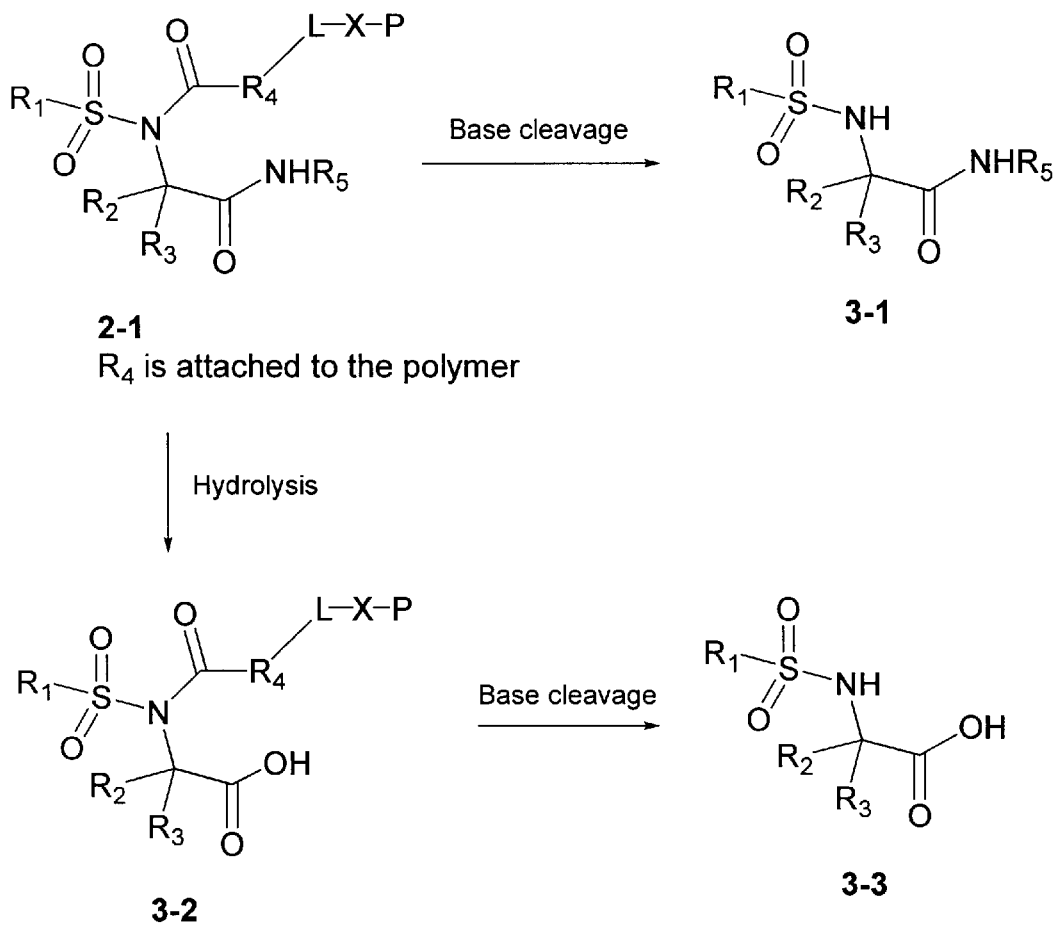
FIG. 3 illustrates cleavage of the product without the acyl moiety where $R_4$ is attached to the solid support.

If $R_4$ of formula 2-1 is attached to the polymer, the polymer-bound intermediate 2-1 is then treated with an appropriate base, such as amine, to cleave the product without the acyl moiety as illustrated in FIG. 3. A free carboxylic acid can be produced by acidic hydrolysis when a convertible isocyanide ($R_5NC$) is used in the first step reaction.

Figure 4:
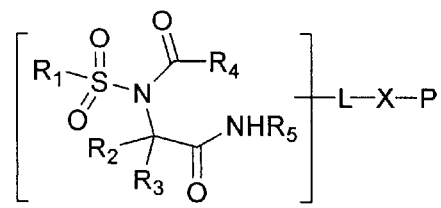
FIG. 4 illustrates cleavage of the product with the acyl moiety where $R_1$, or $R_2$, or $R_5$ is attached to solid support.
Figure 4:
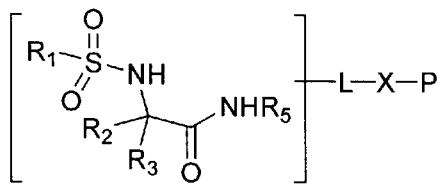
Figure 4:
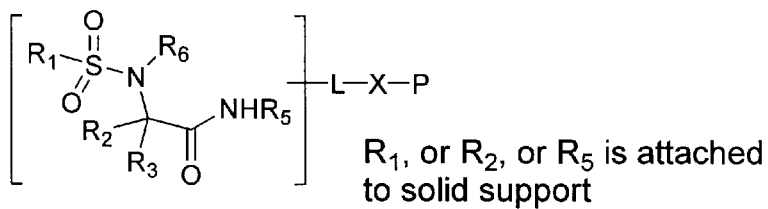
Figure 4:
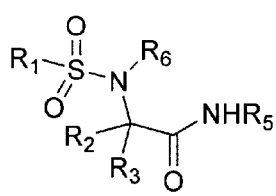

If $R_1$, or $R_2$, or $R_5$ is attached to solid support, the polymer-bound intermediate 2-1 is then treated with an appropriate base, such as amine, to cleave the acyl moiety as illustrated in FIG. 4. An intermediate of formula 4-1 undergoes N-alkylation reaction, such as the Mitsunobu reaction in the presence of $R_6OH$, to give a product of formula 4-2 which is then cleaved under an appropriate condition to afford a product of formula 4-3.

Figure 5:
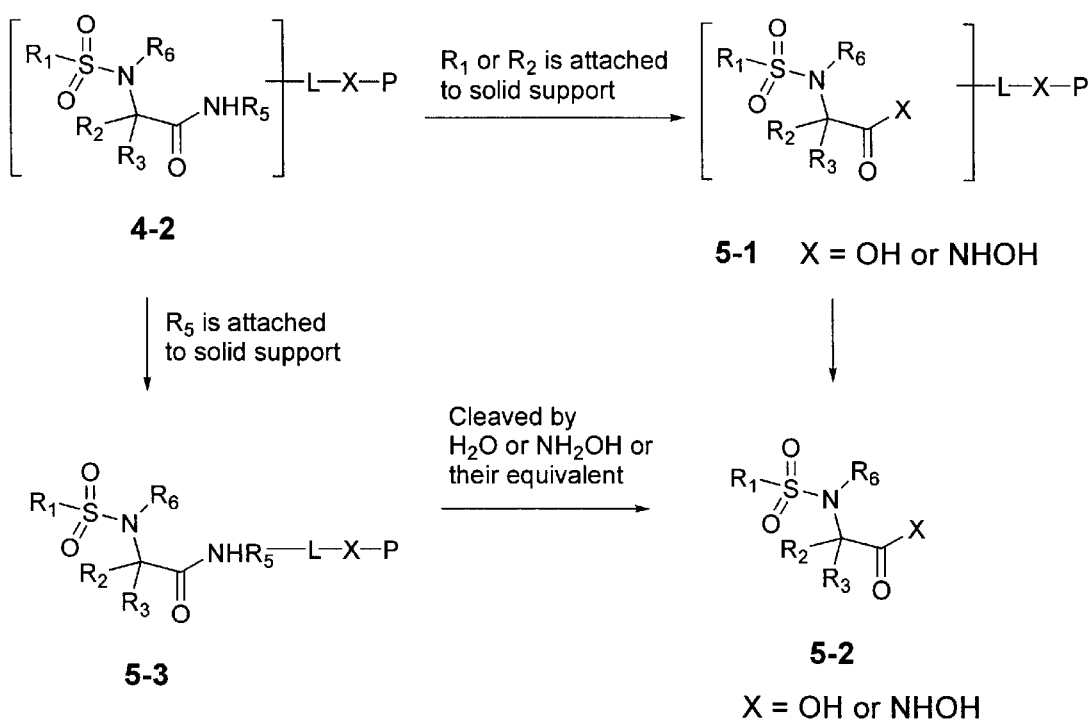
FIG. 5 illustrates the preparation of α-sulfonamido carboxylic acids or the corresponding hydroxamic acids

FIG. 5 illustrates the preparation of α-sulfonamido carboxylic acids or the corresponding hydroxamic acids. A polymer-bound intermediate 4-2 can be transformed to a carboxylic acid or a hydroxamic acid of formula 5-1 if $R_5$ is introduced from a convertible isocyanide. A subsequent cleavage gives the desired acid or hydroxamic acid of formula 5-2. Alternatively, a product of formula 5-2 can be obtained from an intermediate of formula 5-3 in which $R_5$ is attached to the solid support.

The solid support, represented by P, is intended to include the following:

a.) beads, pellets, disks, fibers, gels, or particles such as cellulose beads, pre-glass beads, silica gels, polypropylene beads, polyacrylamide beads, polystyrene beads that are lightly cross-linked with 1–2% divinylbenzene and optionally grafted with polyethylene glycol and optionally functionalized with amino, hydroxy, carboxy or halo groups; and b.) soluble supports such as low molecular weight non-cross-linked polystyrene and polyethylene glycol.

The term solid support is used interchangeably with the term resin or bead in this invention and is intended to mean the same thing.

X is an atom or a functional group connecting the polymer and the linker L, having a structure such as but not limited to oxygen, ester, amide, sulfur, silicon and carbon;

L is a suitable linker, a multifunctional chemical monomer in which one functional group reacts with the polymer to form a covalent bond (X) and the other functional groups react with one of R groups ($R_1$, $R_2$, $R_4$, or $R_5$) through a plurality of chemical reactions to provide the desired templates for further chemistry. Both X and R groups can be represented within a suitable monomer L, such as an amino acid; Commercially available resins, like Wang and Hydroxymethyl polystyrene, are useful in this method. The linkers present in these resins allow the cleavage of final products by a variety of mild chemical conditions that allow isolation of compounds of this invention. The hydroxymethyl polystyrene resin and the Wang resin are examples of solid phase supports used in the preparation of compounds of this invention. Other known or commercially available solid phase supports work in this method and are considered to lie within the scope of this invention.

Solid Support

Solid support is a substrate consisting of a polymer, cross-linked polymer, functionalized polymeric pin, or other insoluble material. These polymers or insoluble materials have been described in literature and are known to those who are skilled in the art of solid phase synthesis (Stewart J M, Young J. D.; Solid Phase Peptide Synthesis, 2nd Ed; Pierce Chemical Company: Rockford. Ill., 1984). Some of them are based on polymeric organic substrates such as polyethylene, polystyrene, polypropylene, polyethylene glycol, polyacrylamide, and cellulose. Additional types of supports include composite structures such as grafted copolymers and polymeric substrates such as polyacrylamide supported within an inorganic matrix such as kieselguhr particles, silica gel, and controlled pore glass.

Examples of suitable support resins and linkers are given in various reviews (Barany, G.; Merrifield, R. B. "Solid Phase Peptide Synthesis", in "The Peptides—Analysis, Synthesis, Biology". Vol 2, [Gross, E. and Meienhofer, J., Eds.], Academic Press, Inc., New York, 1979, pp 1–284; Backes, B. J.; Ellman, J. A. Curr. Opin. Chem. Biol. 1997. 1, 86; James, I. W., Tetrahedron 1999, 55, 4855–4946) and in commercial catalogs (Advanced ChemTech, Louisville, Ky.; Novabiochem, San Diego, Calif.). Some examples of particularly useful functionalized resin/linker combinations that are meant to be illustrative and not limiting in scope are shown below:

(1) Aminomethyl polystyrene resin (Mitchell, A. R., et al., J. Org. Chem., 1978, 43, 2845):

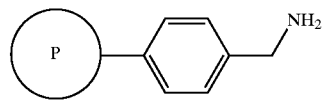

This resin is the core of a wide variety of synthesis resins. The amide linkage can be formed through the coupling of a carboxylic acid to amino group on solid support resin under standard peptide coupling conditions. The amide bond is usually stable under the cleavage conditions for most acid labile, photo labile and base labile or nucleophilic linkers.

(2) Wang resin (Wang, S. S.; J. Am. Chem. Soc. 1973, 95, 1328–1333).

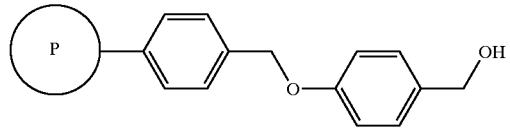

Wang resin is perhaps the most widely used of all resins for acid substrates bound to the solid support resin. The linkage between the substrate and the polystyrene core is through a 4-hydroxybenzyl alcohol moiety. The linker is bound to the resin through a phenyl ether linkage and the carboxylic acid substrate is usually bound to the linker through a benzyl ester linkage. The ester linkage has good stability to a variety of reaction conditions, but can be readily cleaved under acidic conditions, such as by using 25% TFA in DCM.

(3) Rink resin (Rink, H.; Tetrahedron Lett. 1987, 28, 3787).

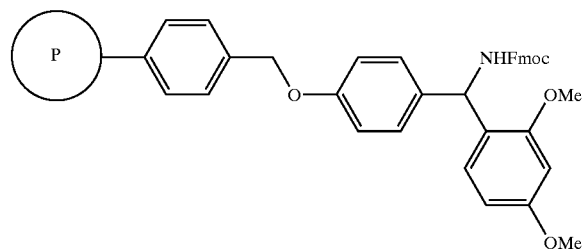

Rink resin is used to prepare amides utilizing the Fmoc strategy. It has also found tremendous utility for a wide range of solid phase organic synthesis protocols. The substrate is assembled under basic or neutral conditions, then the product is cleaved under acidic conditions, such as 10% TFA in DCM.

(4) Knorr resin (Bernatowicz, M. S., et al. Tetrahedron Lett., 1989, 30, 4645).

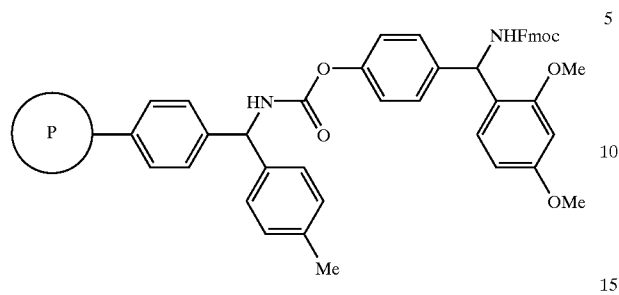

Knorr resin is very similar to Rink resin, except that the linker has been modified to be more stable to TFA.

(5) PAL resin (Bernatowicz, M. S., et al. Tetrahedron lett., 1989, 30, 4645).

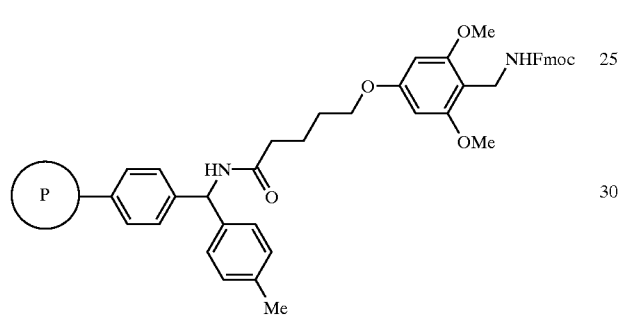

(6) HMBA-MBHA Resin (Sheppard, R. C., et al., Int. J. Peptide Protein Res. 1982, 20, 451).

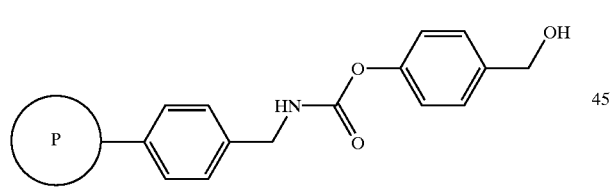

(7) HMPA resin. This also is an acid labile resin which provides an alternative to Wang resin and represented as:

(8) Benzhydrylamine copoly(styrene-1 or 2%-divinylbenzene) which referred to as the BHA resin (Pietta, P. G., et al., J. Org. Chem. 1974, 39, 44).

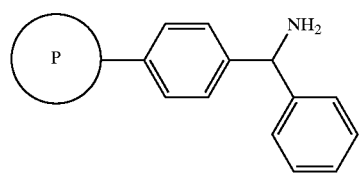

(9) Methyl benzhydrylamine copoly(styrene-1 or 2%-divinylbenzene) which is referred to as MBHA and represented as:

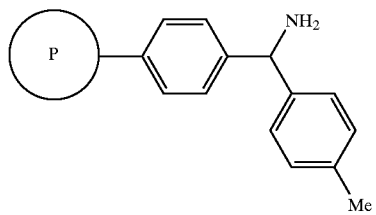

(10) Trityl and functionalized Trityl resins, such as aminotrityl resin and amino-2-chlorotrityl resin (Barlos, K.; Gatos, D.; Papapholiu, G.; Schafer, W.; Wenqing, Y.; Tetrahedron Lett. 1989, 30, 3947).

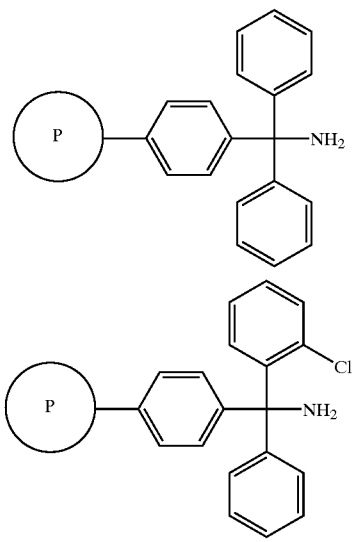

(11) Sieber amide resin (Sieber, P.; Tetrahedron Lett. 1987, 28, 2107).

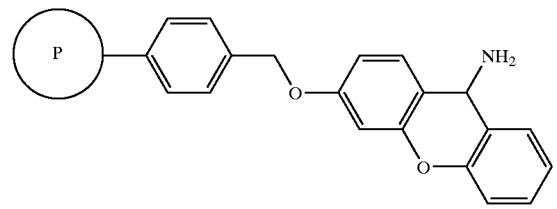

(12) Rink acid resin (Rink, H., Tetrahedron Lett., 1987, 28, 3787).

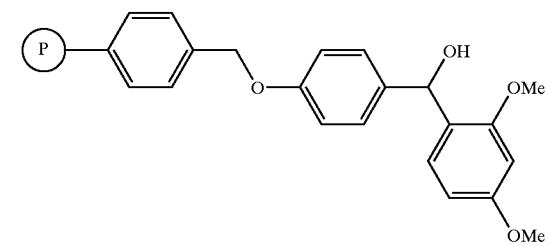

(13) HMPB-BHA resin (4-hydroxymethyl-3-methoxyphenoxybutyric acid-BHA Florsheimer, A.; Riniker, B. in "Peptides 1990; Proceedings of the 21st European Peptide Symposium", [Giralt, E. and Andreu, D. Eds.], ESCOM, Leiden, 1991, pp 131.

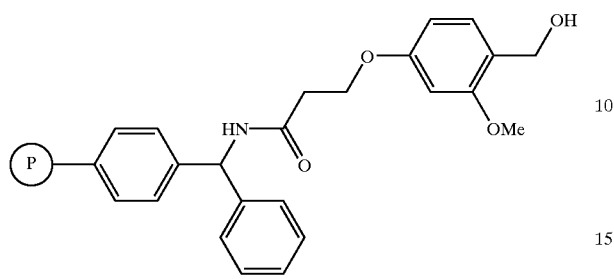

(14) Merrifield resin—Chloromethyl co-poly(styrene-1 or 2%-divinylbenzene) which can be represented as:

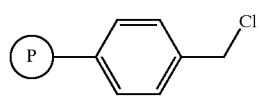

A carboxylic acid substrate is attached to the resin through nucleophilic replacement of chloride under basic conditions. The resin is usually stable under acidic conditions, but the products can be cleaved under basic and nucleophilic conditions in the presence of amine, alcohol, thiol and $H_2O$.

(15) Hydroxymethyl polystyrene resin (Wang, S. S., J. Org. Chem., 1975, 40, 1235).

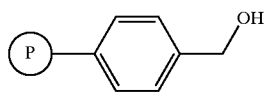

The resin is an alternative to the corresponding Merrifield resin, whereas the substrate is attached to a halomethylated resin through nucleophilic displacement of halogen on the resin, the attachment to hydroxymethylated resins is achieved by coupling of activated carboxylic acids to the hydroxy group on the resin or through Mitsunobu reactions. The products can be cleaved from the resin using a variety of nucleophiles, such as hydroxides, amines or alkoxides to give carboxylic acids, amides and esters.

(16) Oxime resin (DeGrado, W. F.; Kaiser, E. T.; J. Org. Chem. 1982, 47, 3258).

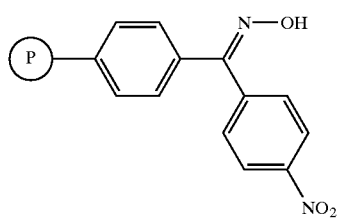

This resin is compatible to Boc chemistry. The product can be cleaved under basic conditions.

(16) Photolabile resins (e.g. Abraham, N. A. et al.; Tetrahedron Lett. 1991, 32, 577). The products can be cleaved from these resins photolytically under neutral or mild conditions, making these resins useful for preparing pH sensitive compounds. Examples of the photolabile resins include:

(a) ANP resin:

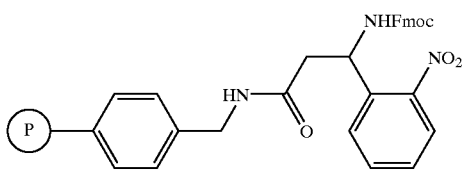

(b) alpha-bromo-alpha-methylphenacyl polystyrene resin:

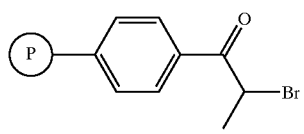

(17) Safety catch resins (see resin reviews above; Backes, B. J.; Virgilio, A. A.; Ellman, J. Am. Chem. Soc. 1996, 118, 3055–6). These resins are usually used in solid phase organic synthesis to prepare carboxylic acids and amides, which contain sulfonamide linkers stable to basic and nucleophilic reagents. Treating the resin with haloacetonitriles, diazomethane, or $TMSCHN_2$ activates the linkers to attack, releasing the attached carboxylic acid as a free acid, an amide or an ester depending on whether the nucleophile is a hydroxide, amine, or alcohol, resepectively. Examples of the safty catch resins include:

(a) 4-sulfamylbenzoyl-4'-methylbenzhydrylamine resin:

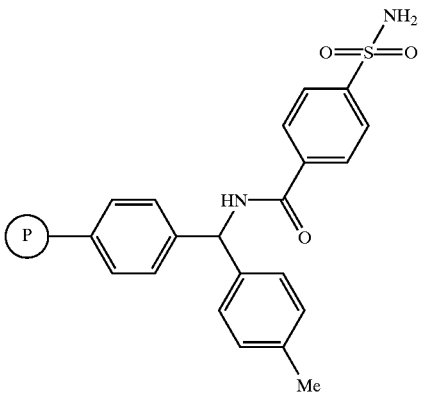

(b) 4-sulfamylbutryl-4'-methylbenzhydrylamine resin:

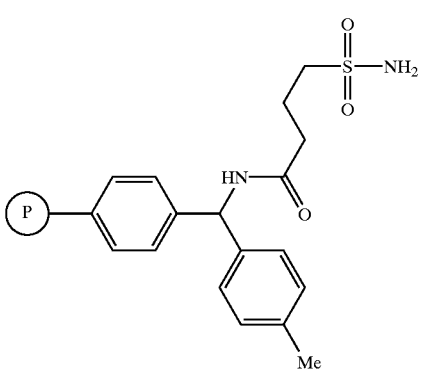

(18) TentaGel resins:

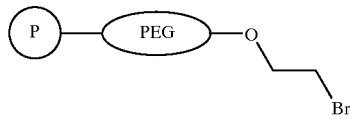

TentaGel resins are polyoxycthyleneglycol (PEG) grafted (Tentagel) resins (Rapp, W.; Zhang, L.; Habich, R.; Bayer, E. in "Peptides 1988; Proc. 20$^{rth}$ European Peptide Symposium" [Jung, G. and Bayer, E., Eds.], Walter de Gruyter, Berlin, 1989, pp 199–201. TentaGel resins, e.g. TentaGel S Br resin can swell in a wide variety of solvents and the bead size distribution is very narrow, making these resins ideal for solid phase organic synthesis of combinatorial libraies. TentaGel S Br resin can immobilize carboxylic acids by displacing the bromine with a carboxylic acid salt. The products can be released by saponification with dilute aqueous base.

(19) Resins with silicon linkage (Chenera, B.; Finkelstein, J. A.; Veber, D. F.; J. Am. Chem. Soc. 1995, 117, 11999–12000; Woolard, F. X.; Paetsch, J.; Ellman, J. A.; J. Org. Chem. 1997, 62, 6102–3). Some examples of these resins contain protiodetachable arylsilane linker and traceless silyl linker. The products can be released in the presence of fluoride.

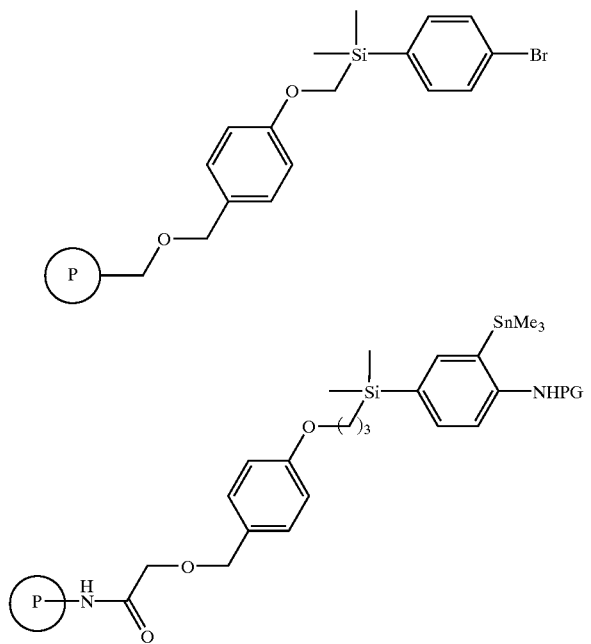

Also useful as a solid phase support in the present invention are solubilizable resins that can be rendered insoluble during the synthesis process as solid phase supports. Although this technique is frequently referred to as "Liquid Phase Synthesis", the critical aspect for our process is the isolation of individual molecules from each other on the resin and the ability to wash away excess reagents following a reaction sequence. This also is achieved by attachment to resins that can be solubilized under certain solvent and reaction conditions and rendered insoluble for isolation of reaction products from reagents. This latter approach, (Vandersteen, A. M.; Han, H.; Janda, K. D.; Molecular Diversity, 1996, 2, 89–96.) uses high molecular weight polyethyleneglycol as a solubilizable polymeric support and such resins are also used in the present invention.

EXAMPLES

The following examples (Schemes 6, 7 and 8) are by way of illustration of various aspects of the present invention and are not intended to be limiting thereof.

General Procedures-Reagent Systems and Test Methods

Anhydrous solvents were purchased from Aldrich Chemical Company and used directly. Resins were purchased from Advanced ChemTech, Louisville, Ky., and used directly. The loading level ranged from 0.60 to 1.0 mmol/g. Unless otherwise noted, reagents were obtained from commercial suppliers and used without further purification. Preparative thin layer chromatography was preformed on silica gel pre-coated glass plates (Whatman PK5F, 150 Å, 1000 μm) and visualized with UV light, and/or ninhydrin, p-anisaldehyde, ammonium molybdate, or ferric chloride. NMR spectra were obtained on a Varian Mercury 500 MHz spectrometer. Chemical shifts are reported in ppm. unless otherwise noted, spectra were obtained in CD$_3$OD with residual CH$_3$OH as an internal standard at 7.26 ppm. IR spectra were obtained on a Midac M1700 and absorbencies are listed in inverse centimeters. HPLC/MS analysis were performed on a Hewlett Packard 1100 with a photodiode array detector coupled to a Micros Platform II electrospray mass spectrometer. An evaporative light scattering detector (Sedex 55) was also incorporated for more accurate evaluation of sample purity. Reverse phase columns were purchased from YMC, Inc. (ODS-A, 3 μm, 120 Å, 4.0×50 mm).

Solvent system A consisted of 97.5% MeOH, 2.5% H$_2$O, and 0.05% TFA. Solvent system B consisted of 97.5% H$_2$O, 2.5% MeOH, and 0.05% TFA. Samples were typically acquired at a mobile phase flow rate of 2 ml/min involving a 2 minute gradient from solvent B to solvent A with 5 minute run times. Resins were washed with appropriate solvents (100 mg of resin/1 ml of solvent). Technical grade solvents were used for resin washing.

Scheme 6

Example 1

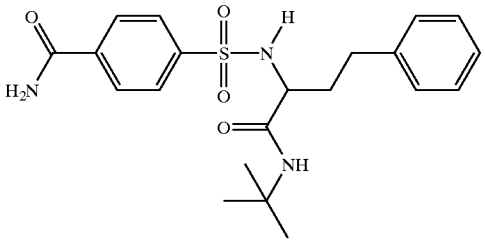

Example 2

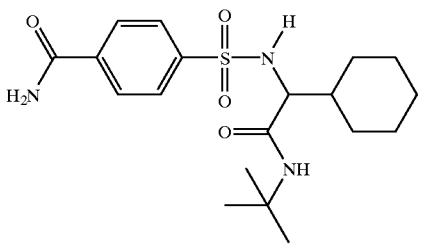

Example 3
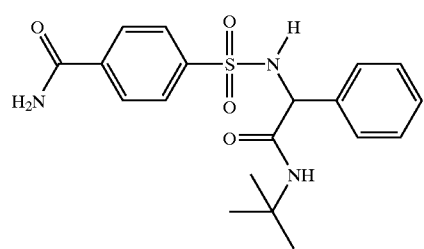
Example 4
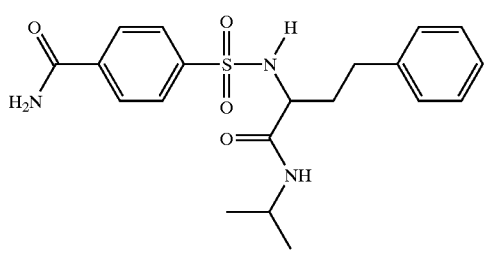
Example 5
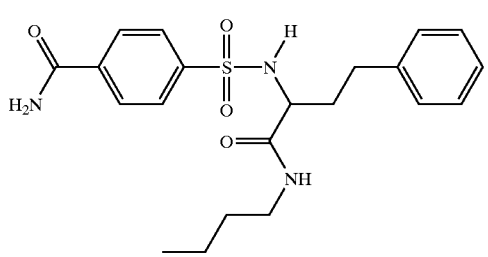
Example 6
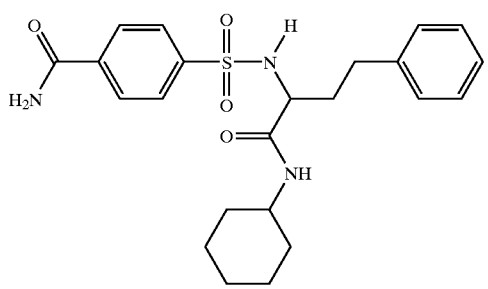
Example 7
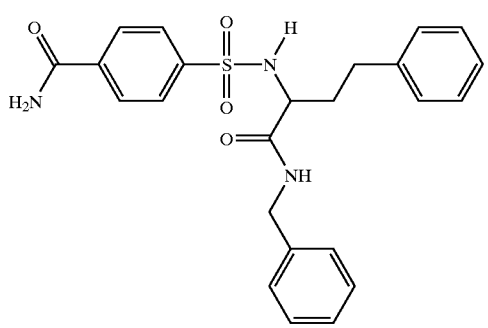
Scheme 7
Example 8
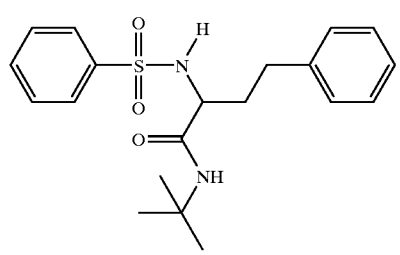
Example 9
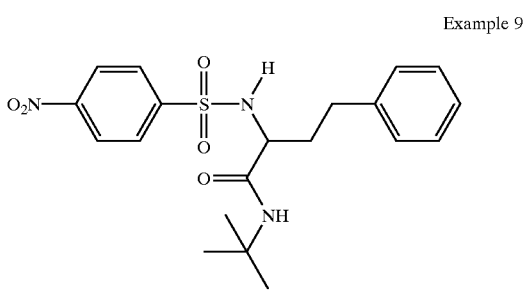
Example 10
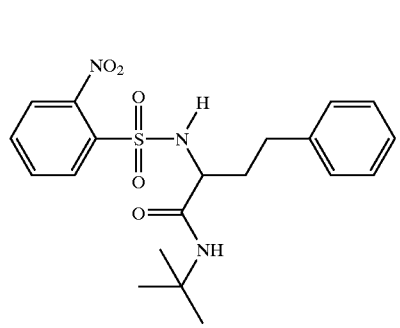
Example 11
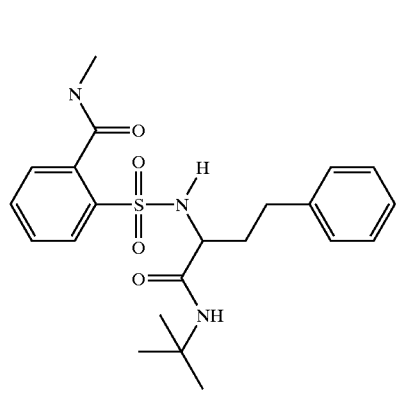
Example 12
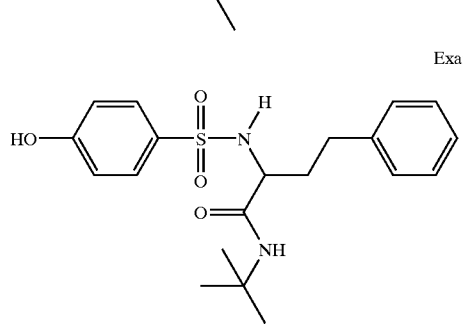

Example 13
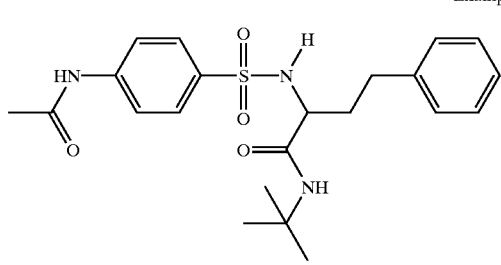
Example 14
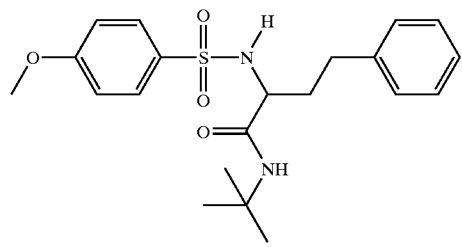
Scheme 8
Example 15
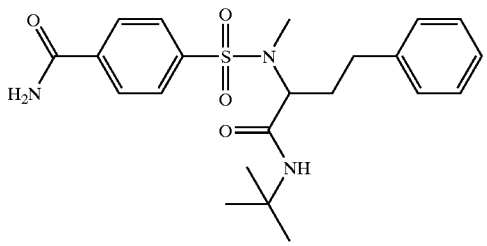
Example 16
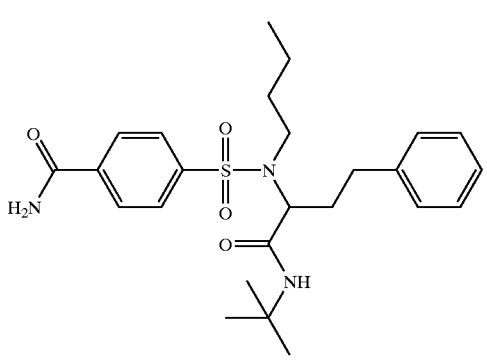
Example 17
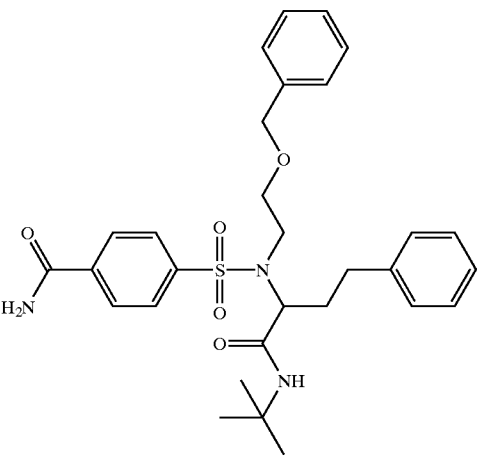
Example 18
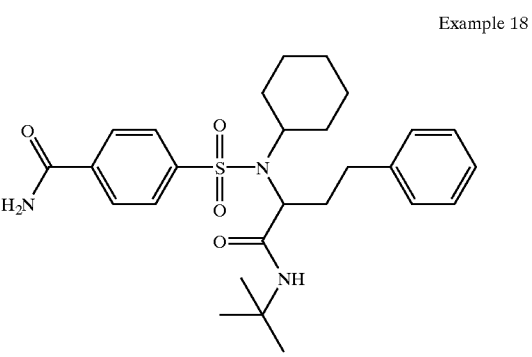
Example 1
t-Butyl 2-(4-aminocarbonylbenzenesulfonamido)-4-phenyl-butyramide
Preparation of Aminosulfonylbenzamide Rink Resin (9-1)
Scheme 9
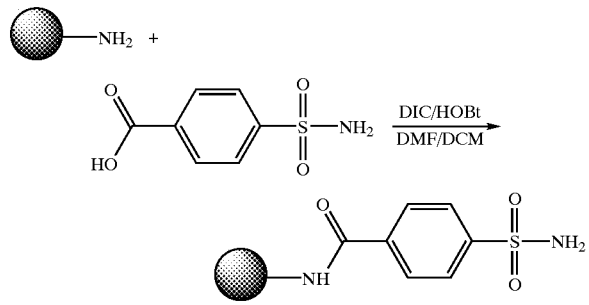

In a 250 mL reaction vessel of an ACT 90 peptide synthesizer, 5 g of Rink resin (4 mmol, 0.8 mmol/g) was introduced. The resin was treated with 50 mL of 20% piperidine in DMF (30 min, room temperature) to remove the Fmoc protecting group. The excess of the reagent was removed by filtration and the resin was washed with DMF (2×25 mL) then with methanol (1×25 mL) and DCM (3×25 mL). To the resin was added 24 mL (6 eq.) solution of 4-carboxybenzenesulfonamide (1.0M in DMF) containing equimolar amount (6 eq.) of HOBt. The resin suspension was then mixed for 2 h. The reagent solution was removed by filtration and the resin was washed and dried as previously mentioned. Negative Kaiser test indicated complete conversion. Loading of the obtained resin, determined by TFA cleavage of a resin sample, was 0.5 mmol/g.

(10eq., 1.0 M solution in MeOH), 50 mL of acetic acid solution (10 eq., 1.0 M in THF), and 5 mL of t-butyl isocyanide solution (10 eq., 1.0 M in MeOH) were added. The suspension was mixed on an ACT Labmate at 60° C. for 24 h. Then, the excess of the reagent solution was removed by filtration and the resin was washed and dried. The acetyl group was removed by treatment with a mixture of 48% aqueous methylamine solution and THF (10 mL, 1:1) overnight at room temperature. The desired sulfonamide was cleaved by treatment with TFA (25% solution in DCM) for 30 minutes. The product was isolated by evaporation of the TFA solution. $^1$HNMR (CD$_3$OD): δ 7.94–8.11 (m, 4H), 7.10–7.32 (m, 5H), 3.78–3.85 (m, 1H), 2.73 (m, 1H), 2.61 (m, 1H), 1.94 (m, 1H), 1.86 (m, 1H), 1.15 (s, 9H).

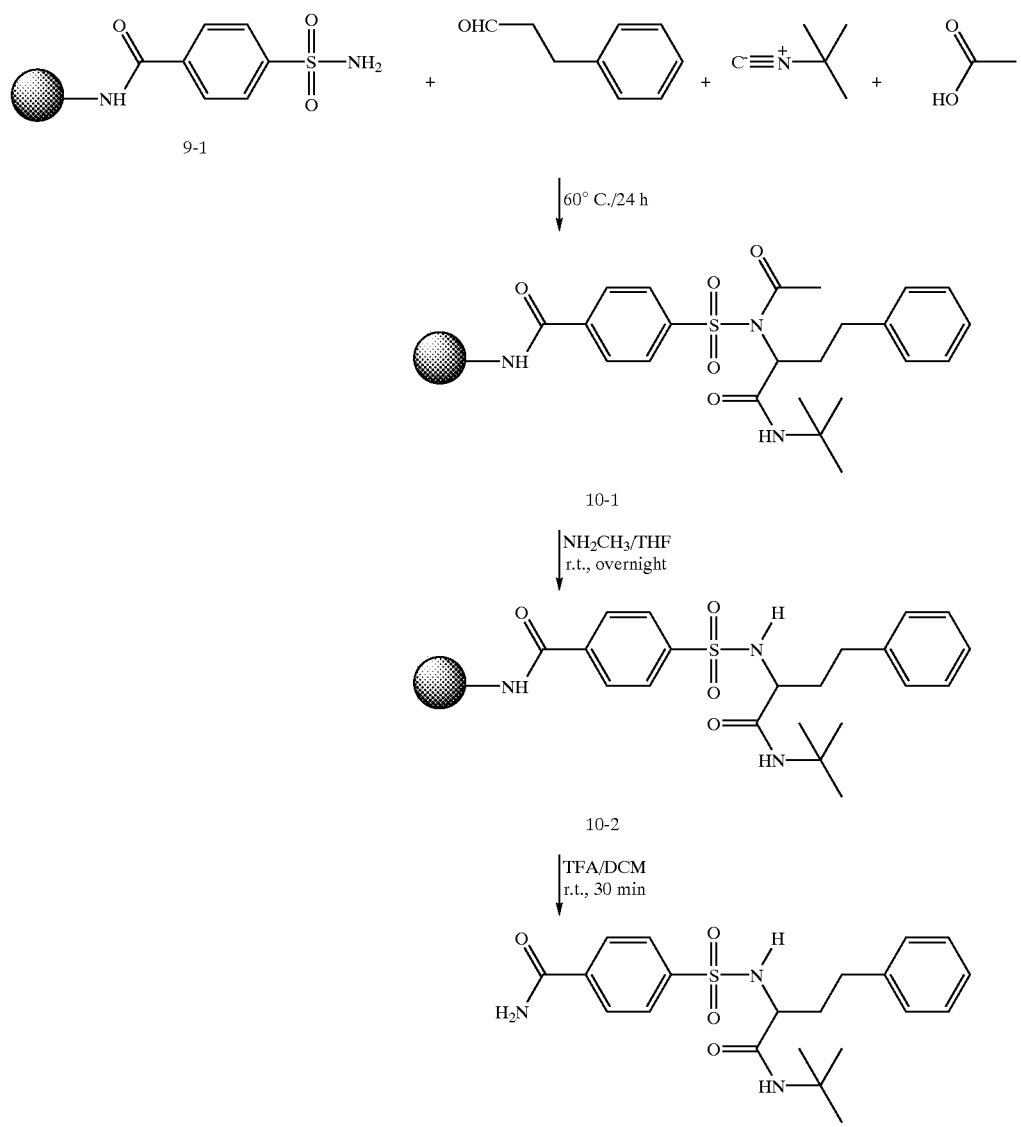

As illustrated in Scheme 10, aminosulfonylbenzamide Rink resin (9-1) was used as amine component in Ugi reaction for the synthesis of substituted sulfonamides (Example 1). The resin (1 g, 0.5 mmol) in a 40 ml vial was swelled with 5 mL THF. Then 5 mL of 3-phenylpropanal Example 2
t-Butyl 2-(4-aminocarbonylbenzenesulfonamido)-2-cyclohexylacetamide The same procedure described for the preparation of Example 1 was followed except that cyclohexanecarboxaldehyde was used instead of 3-phenylpropanal. LC-MS analysis showed that the purity of the final cleaved product was more than 80%.

Example 3 t-Butyl 2-(4-aminocarbonylbenzenesulfonamido)-2-phenyl-acetamide

The same procedure described for the preparation of Example 1 was followed except that benzaldehyde was used instead of 3-phenyl propanal. $^1$HNMR (CD$_3$OD): δ 7.95 (d, J=8 Hz, 2H), 7.88 (d, J=8 Hz, 2H), 7.23–7.26 (m, 5H), 4.94 (s, 1H), 1.14 (s, 9H).

Example 4 iso-Propyl 2-(4-aminocarbonylbenzenesulfonamido)-4-phenylbutyramide

The same procedure described for the preparation of Example 1 was followed except that isopropyl isocyanide was used instead of t-butyl isocyanide. $^1$HNMR (CD$_3$OD): δ 8.01 (d, J=8.5 Hz, 2H), 7.92 (d, J=8.5 Hz, 2H), 7.08–7.22 (m, 5H), 3.73–376 (dd,1H), 3.62–367 (m, 1H), 2.62–2.68 (m, 1H), 2.48–2.54 (m, 1H), 1.78–1.89 (m, 2H), 0.99 (d, J=6.5 Hz, 3H).

Example 5 n-Butyl 2-(4-aminocarbonylbenzenesulfonamido)-4-phenyl-butyramide

The same procedure described for the preparation of Example 1 was followed except that n-butyl isocyanide was used instead of t-butyl isocyanide. $^1$HNMR (CD$_3$OD): δ 8.01 (d, J=8 Hz, 2H), 7.91 (d, J=8 Hz, 2H), 7.06–7.22 (m, 5H), 4.21 (dd, 1H), 2.91(m, 2H), 2.60 (m, 1H), 2.50 (m, 1H), 0.87–1.80 (m, 9H).

Example 6

Cyclohexyl 2-(4-aminocarbonylbenzenesulfonamido)-4-phenylbutyramide

The same procedure described for the preparation of Example 1 was followed except that cyclohexyl isocyanide was used instead of t-butyl isocyanide. $^1$HNMR (CD$_3$OD): δ 8.00 (d, J=8.5 Hz, 2H), 7.86(d, J=8.5 Hz, 2H), 7.09–7.24 (m, 5H), 3.75–3.77 (dd, 1H), 3.28 (m, 1H), 2.63–2.68 (m, 1H), 2.49–2.55 (m, 1H), 0.90–1.90 (m, 12H).

Example 7

Benzyl 2-(4-aminocarbonylbenzenesulfonamido)-4-phenyl-butyramide

The same procedure described for the preparation of Example 1 was followed except that benzyl isocyanide was used instead of t-butyl isocyanide. $^1$HNMR (CD$_3$OD): δ 7.98 (d, J=8 Hz, 2H), 7.91 (d, J=8 Hz, 2H), 7.03–7.27 (m, 10H), 4.16 (d, J=12 Hz, 1H), 4.10 (d, J=12 Hz, 1H), 3.81 (m, 1H), 1.35 (m, 2H)., 0.92 (m, 2H).

Example 8 t-Butyl 2-benzenesulfonamido-4-phenylbutyramide

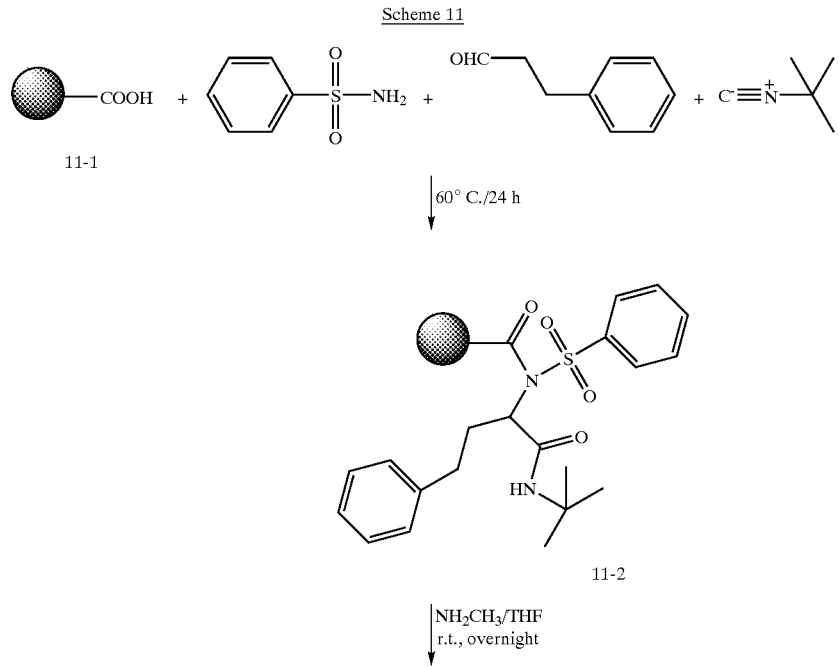

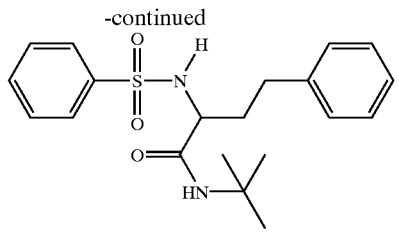

The preparation of Example 8 is illustrated in Scheme 11, in an 8 mL vial carboxypolystyrene resin (11-1) (100 mg) was swelled in 2 mL of THF. Then 2 mL of benzenesulfonamide solution (10 equiv., 1.0 M in THF), 2 mL of 3-phenylpropanal solution (10 equiv., 1.0 M in MeOH), and 2 mL of t-butyl isocyanide solution (10 equiv., 1.0 M in MeOH) were added. The suspension was mixed on an ACT Labmate at 60° C. for 24 h. Then the excess of reagent solution was removed by filtration and the resin (11-2) was washed and dried. The desired product was cleaved by treatment with a mixture of 48% aqueous methylamine and THF (2 mL, 1:1) for 12 h at room temperature. $^1$HNMR (CD$_3$OD): δ 7.53–7.87 (m, 5H), 7.08–7.24 (m, 5H), 3.74 (t, 1H), 2.64(m, 1H), 2.48(m, 1H), 1.86 (m, 1H), 1.75 (m, 1H), 1.14 (s, 9H).

Example 9 t-Butyl 2-(4-nitrobenzenesulfonamido)-4-phenylbutyramide

The same procedure described for the preparation of Example 8 was followed except that 4-nitrobenzensulfonamide was used instead of benzenesulfonamide. $^1$HNMR (CD$_3$OD): δ 8.35–7.13 (m, 9H), 3.894 (m, 1H), 2.64(m, 1H), 2.69(t, 2H), 2.01 (m, 1H), 1.82 (m, 1H), 1.75 (m, 1H), 1.36(s, 9H).

Example 10 t-Butyl 2-(2-nitrobenzenesulfonamido)-4-phenyl-butyramide

The same procedure described for the preparation of Example 8 was followed except that 2-nitrobenzensulfonamide was used instead of benzenesulfonamide. $^1$HNMR (CD$_3$OD): δ 8.08 (d, J=8 Hz, 1H), 7.91(d, J=8 Hz, 1H), 7.74–7.83 (m, 2H), 7.13–7.25 (m,5H), 3.92 (m, 1H),2.71 (m, 1H), 2.58(m, 1H), 1.95 (m, 1H), 1.88 (m, 1H), 1.11 (s, 9H).

Example 11 t-Butyl 2-[2-(methylaminocarbonyl)benzenesulfonamido]-4-phenylbutyramide

The same procedure described for the preparation of Example 8 was followed except that 2-(methoxycarbonyl)-benzensulfonamide was used instead of benzenesulfonamide. $^1$HNMR (CD$_3$OD): δ 7.93 (d, J=8 Hz, 1H), 7.73(d, J=8 Hz, 1H), 7.55–7.62 (m, 2H), 7.09–7.23 (m,5H), 3.82 (t, 1H),2.71 (m, 1H), 2.94(m, 3H), 2.68 (m, 1H), 2.55(m, 1H), 1.90 (m, 1H), 1.83 (m, 1H), 1.11 (s, 9H).

Example 12 t-Butyl 2-(4-hydroxybenzenesulfonamido)-4-phenyl-butyramide

The same procedure described for the preparation of Example 8 was followed except that 4-hydroxybenzensulfonamide was used instead of benzenesulfonamide. $^1$HNMR (CD$_3$OD): δ 7.67–7.69 (m, 2H), 7.21–7.22 (m, 2H), 7.12–7.15 (m, 1H), 3.66 (t, 1H),2.64 (m, 1H), 2.49 (m, 1H), 1.85 (m, 1H), 1.74 (m, 1H), 1.17 (s, 9H).

Example 13 t-Butyl 2-(4-acetamidobenzenesulfonamido)-4-phenyl-butyramide

The same procedure described for the preparation of Example 8 was followed except that 4-acetamidobenzensulfonamide was used instead of benzenesulfonamide. LC-MS analysis indicated that the desired product was obtained in more than 80% purity.

Example 14 t-Butyl 2-(4-methoxybenzenesulfonamido)-4-phenyl-butyramide

The same procedure described for the preparation of Example 8 was followed except that 4-methoxybenzensulfonamide was used instead of benzenesulfonamide. LC-MS analysis indicated that the desired product was obtained in more than 80% purity.

Example 15 t-Butyl 2-[N-methyl-N-(4-aminocarbonyl)-benzenesulfonyl]amino-4-phenylbutyramide Scheme 12

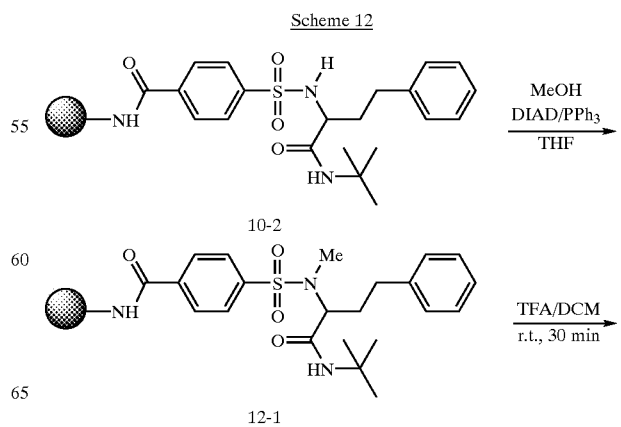

-continued

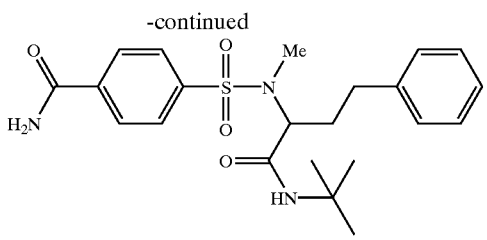

Preparation of Example 15 is illustrated in Scheme 12, the resin intermediate (10⁻²) was alkylated with benzyl alcohol under the Mitsunobu reaction conditions. The resin (10⁻²) (200 mg) was introduced into an 8 mL vial. To it were added 1 mL of methanol solution (10 equiv., 1.0 M in THF), 1 mL of triphenylphosphine solution (10 equiv., 1.0 M in THF), and 1 mL of DIAD solution (10 equiv., 1.0 M in THF). The suspension was mixed on an ACT Labmate at room temperature for 5 h. Then the excess of the reagent solution was removed by filtration; the resin (12-1) was washed and dried. Sulfonamide (Example 15) was cleaved by treatment with 25% TFA in DCM for 30 min at room temperature. $^1$HNMR (CD$_3$OD): δ 8.04 (d, J=7 Hz, 2H), 7.89 (d, J=7 Hz, 2H), 7.11–7.38 (m, 5H), 4.38 (t, 1H), 3.00 (s, 3H), 2.50 (t, 2H), 1.97–2.01 (m, 1H), 1.70–1.74 (m, 1H), 1.21 (s, 9H).

Example 16 t-Butyl 2-[N-butyl-N-(4-aminocarbonyl)-benzene-sulfonyl]amino-4-phenylbutyramide The same procedure described for the preparation of Example 15 was followed except that n-butyl alcohol was used instead of methonal. $^1$HNMR (CD$_3$OD): δ 8.00–8.02 (d, J=8.5 Hz, 2H), 7.83–7.85 (d, J=8.5 Hz, 2H), 7.03–7.25 (m, 5H), 4.21 (m, 1H), 3.55(m, 1H), 3.24 (m, 1H), 1.52–2.50 (m, 8H), 1.27 (s, 9H), 0.92 (t, 3H).

Example 17 t-Butyl 2-[N-(2-benzyloxyethyl)-N-(4-aminocarbonyl)-benzenesulfonyl]amino-4-phenylbutyramide The same procedure described for the preparation of Example 15 was followed except that benzyloxyethyl alcohol was used instead of methonal. $^1$HNMR (CD$_3$OD): δ 8.00 (d, J=8 Hz, 2H), 7.88(d, J=8 Hz, 2H), 6.99–7.32 (m, 10 H), 4.45–4.53 (dd, J=11.50 Hz, 2H), 4.21–4.24 (m, 1H), 3.80 (m, 1H), 3.68 (m, 2H), 3.53–3.56 (m, 1H), 1H), 2.46 (m, 2H), 2.06 (m, 1H), 1.68 (m, 1H), 1.21 (s, 9H).

Example 18 t-Butyl 2-[N-cyclohexyl-N-(4-aminocarbonyl)-benzene-sulfonyl]amino-4-phenylbutyramide The same procedure described for the preparation of Example 15 was followed except that cyclohexyl alcohol was used instead of methonal. $^1$HNMR (CD$_3$OD): δ 7.90 (d, J=8 Hz, 2H), 7.86(d, J=8 Hz, 2H), 7.001–7.25 (m, 5H), 3.99 (m, 1H), 3.54(m, 1H), 1.30–2.50 (m, 14H), 1.32 (s, 9H).

As will be understood by those skilled in the art, various arrangements which lie within the spirit and scope of the invention other than those described in detail in the specification will occur to those persons skilled in the art. It is therefor to be understood that the invention is to be limited only by the claims appended hereto. Accordingly,

We claim:

1. A method for synthesizing α-sulfonamido amide, α-sulfonamido carboxylic acid and α-sulfonamido hydroxamic acid derivatives comprising carrying out a four component condensation reaction between components consisting of a sulfonamide, an aldehyde or ketone, an isocyanide and a carboxylic acid, one of said components being attached to a solid support.

2. The method of claim 1 wherein said derivative has the formula:

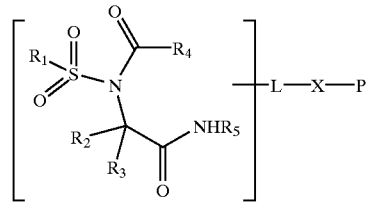

2-1 where;

R$_1$, R$_2$, R$_3$, R$_4$, or R$_5$ are selected from an organic substituent,

P is said solid support,

L is a multifunctional monomer carrying a first functional group that forms a covalent bond X and a second functional group that forms a covalent bond with one of R$_1$, R$_2$, R$_3$, R$_4$, or R$_5$ X is a covalent bond to join L and P.

3. The method of claim 1 wherein said component attached to said solid support is an aldehyde or ketone.

4. The method of claim 1 wherein said component attached to said solid support is an isocyanide.

5. The method of claim 1 wherein said component attached to said solid support is a carboxylic acid.

6. The method of claim 1 wherein said component attached to said solid support is an α-sulfonamide.

* * * * *